United States Patent [19]

Nohl et al.

[11] Patent Number: 5,238,654
[45] Date of Patent: Aug. 24, 1993

[54] SYRINGE DRIVE WITH LEAD SCREW MECHANISM

[75] Inventors: Andre Nohl, Sunnyvale; Thomas J. McCall, Jr., Fremont, both of Calif.

[73] Assignee: Spectra-Physics Analytical, Inc., Fremont, Calif.

[21] Appl. No.: 891,780

[22] Filed: Jun. 1, 1992

[51] Int. Cl.$^5$ ............................ B01L 3/02; F16H 1/14
[52] U.S. Cl. ................................. 422/100; 73/864.01; 74/424.8 R; 74/424.8 A; 604/187; 128/DIG. 1
[58] Field of Search .................... 422/100; 73/864.01; 128/DIG. 1; 604/187; 74/424.8 R, 424.8 A

[56] References Cited

U.S. PATENT DOCUMENTS

| | | | |
|---|---|---|---|
| 4,475,666 | 10/1984 | Bilbrey et al. | 222/14 |
| 4,476,999 | 10/1984 | Bilbrey | 222/75 |
| 4,528,158 | 7/1985 | Gilles et al. | 422/63 |
| 4,528,161 | 7/1985 | Eckert | 422/101 |
| 4,544,369 | 10/1985 | Skakoon et al. | 604/155 |
| 4,622,457 | 11/1986 | Bradley et al. | 235/464 |
| 4,957,009 | 9/1990 | Nohl et al. | 73/864.84 |
| 5,101,679 | 4/1992 | Smith et al. | 74/424.8 |

Primary Examiner—James C. Housel
Assistant Examiner—N. Bhat
Attorney, Agent, or Firm—Killworth, Gottman, Hagan & Schaeff

[57] ABSTRACT

A syringe of relatively simple construction which is capable of both accurate and reproducible sample volume withdrawals, including volumes of 1.0 μl or less, is provided. The syringe drive mechanism is preferably adapted for use in a liquid sampling apparatus and includes a threaded lead screw, a drive for rotating the screw, and a syringe having a plunger for withdrawing a liquid sample. The plunger is mechanically connected to the rotating lead screw by a nut threaded onto the screw and a slider mechanism associated with the nut which also is secured to the plunger. The nut is designed so that lateral misalignment of the drive screw does not affect the precise linear movement of the slider mechanism, and consequently, the plunger. This provides a mechanism which is less expensive to assemble and align properly, but which has a high degree of accuracy and reproducibility.

18 Claims, 4 Drawing Sheets

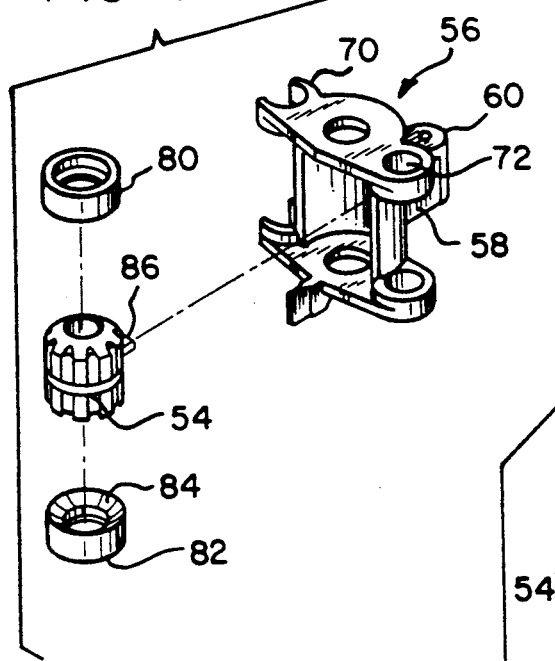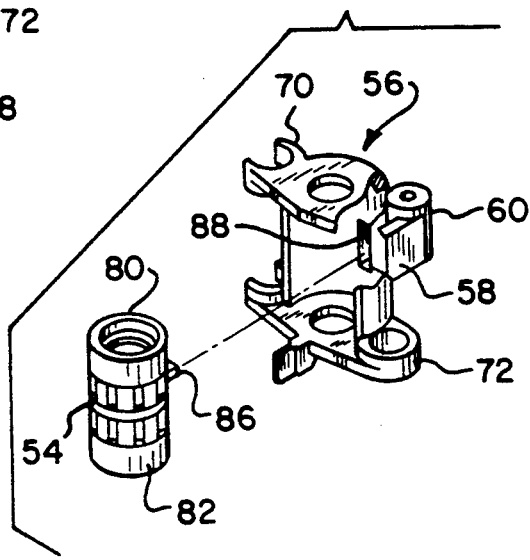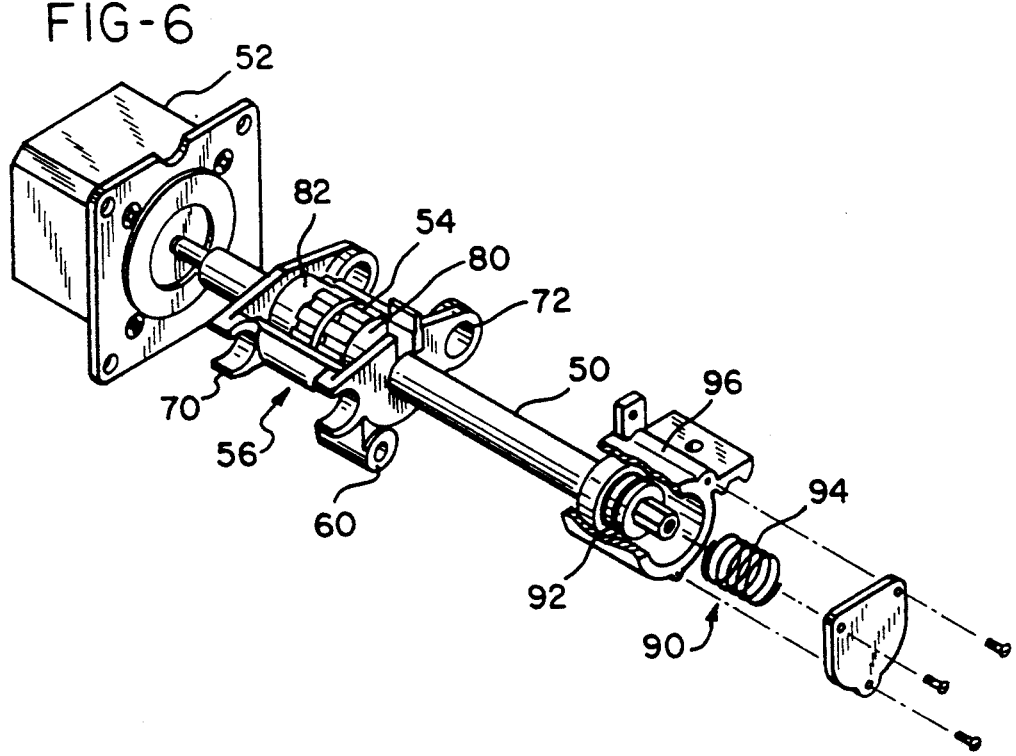

SYRINGE DRIVE WITH LEAD SCREW MECHANISM

BACKGROUND OF THE INVENTION

This invention relates to liquid sampling techniques and devices for taking accurate and reproducible liquid sample volumes, and in particular to a syringe drive with a lead screw mechanism for use in an autosampler system which itself may be used in conjunction with a liquid chromatograph.

In liquid chromatography systems, automated sampling equipment has been developed and used for analyzing multiple samples. Small volumes of liquid samples are automatically withdrawn from sample containers and then injected into liquid chromatography columns for separation and analysis. Such an automated mechanism is described in U.S. Pat. No. 4,622,457 to Bradley et al, issued Nov. 11, 1986, the disclosure of which is hereby incorporated by reference.

The trend in liquid chromatography analysis has been toward the use of smaller and smaller samples. Today, typical sample volumes may be in the range of 10–50 $\mu l$, but may range down to as little as 1.0 $\mu l$ or less. With the small sample volumes analyzed, it has become critical that the sampling mechanism not only be accurate in the volume taken, but also produce reproducible results. That is, from one sample to the next, the sampling mechanism must be able to withdraw and deliver the same volume, or whatever volume is preselected, time after time.

A number of mechanisms have been used in the prior art for withdrawing samples from sample containers. These include both purge mechanisms and syringe mechanisms. Purge mechanisms operate by purging a sample loop. However, purge mechanisms tended to be uncontrolled. That is, gas pressurization or suction alone has been relied on to move a sample volume from its container into the sample loop. Generally, such mechanisms may be used with a complete fill loop only, where the sample taken completely filled a predetermined volume in a sample loop.

Syringe transport mechanisms have also been used to withdraw a sample volume from a container. Typically, the syringe is physically inserted into the sample container, a predetermined sample volume is drawn into the syringe, and the syringe is then removed from the sample container. The syringe containing the sample is then physically moved and connected to a sample injection mechanism for injecting the sample into a chromatography column or other separation device or detector. Newer syringe and automated sampler designs have utilized multiport valves so that the sample may be drawn directly into a sample loop by the syringe.

The use of a syringe to withdraw a sample offers the benefit of a low waste level. Only the small volume of sample needed is withdrawn. However, prior syringe mechanisms have had a number of problems which have affected accuracy and reproducibility. Generally, the syringe includes a plunger which is mechanically connected to a stepper motor through a lead screw drive mechanism. Lead screw mechanisms have not provided perfectly linear motion, due either to slight manufacturing defects such as a bent lead screw or misalignment occurring during assembly or in use. Rather, typically there is a cyclic modulation of the linear displacement of the mechanism.

With the advent of sample volumes of only a fraction of a microliter, less than one complete rotation of the screw drive is needed. Thus, for a 0.5 $\mu l$ sample, the screw drive may turn less than one-quarter of a full rotation. Any misalignment of the screw drive with respect to the plunger, even if small, may introduce significant errors into the sample volume and/or the ability to reproduce the same sample volume repeatedly. This increases the costs of manufacturing and assembling the syringe drive because of the need for strict tolerances to minimize any misalignment. Moreover, over time, the drive mechanism will wear and introduce an additional degree of wobble or misalignment. Even if perfectly aligned initially, the mechanism may become misaligned through movement of equipment and the concomitant bumping and jarring of the mechanism which is inevitable during use. Misalignment also increases stress on the mechanism which may result in excess wear.

While it may be possible to attempt to use lead screw mechanisms having a much greater number of threads per inch to improve accuracy during operation, such screws may be prohibitively expensive to manufacture and may themselves include small manufacturing defects. However, misalignment would remain a problem. Accordingly, there is a need in the art for a relatively simple and inexpensive syringe drive with a lead screw mechanism which permits both accurate and reproducible sample withdrawals.

SUMMARY OF THE INVENTION

The present invention meets that need by providing a syringe of relatively simple construction which is capable of both accurate and reproducible sample volume withdrawals, including volumes of 1.0 $\mu l$ or less. The syringe drive mechanism of the present invention is preferably adapted for use in an autosampler in conjunction with a liquid chromatography analysis system. However, it may find use in other sampling systems where accuracy and reproducibility in the handling of small liquid volumes are required.

In accordance with one aspect of the present invention, a syringe drive mechanism for use in a sampling apparatus is provided which includes a threaded lead screw, means for rotating the screw, a syringe having a plunger for withdrawing a liquid sample, and means for mechanically connecting the plunger to the screw. The screw is driven and caused to rotate by a motor. A stepper motor is preferred because such a motor provides the precise starting and stopping of the rotation of the screw which is needed for accurate sample withdrawals.

The connecting means for the plunger which mechanically connects the plunger to the rotating lead screw comprises a nut threaded onto the screw, a slider mechanism associated with the nut which also includes means for securing the plunger thereto, means for aligning the slider mechanism for linear movement, and means for permitting lateral movement of the nut. Preferably, the means for aligning the slider mechanism comprises a pair of substantially parallel rails and means for slidably securing the slider to the rails. As the lead screw is rotated, the nut which is threaded thereon and which is associated with the slider mechanism is caused to translate linearly with the slider. Linear movement of the slider causes a corresponding linear movement of the plunger on the syringe mechanism.

During linear movement of the nut and slider, the nut is also permitted to move laterally. The means for permitting this lateral movement of the nut includes at least one bearing having an annular opening therein for the screw to pass through. Preferably a pair of bearings are provided, with each bearing positioned on opposite ends of the nut. The bearings include hemispherical inner surfaces adapted to mate with correspondingly-shaped exterior surfaces of the nut to permit lateral movement of the nut.

To prevent rotation of the nut around the lead screw, means are preferably associated with the nut comprising a tab extending laterally from the nut. The slider includes a recess therein for receiving the laterally extending tab from the nut, locking the nut in place and preventing rotation thereof during its linear travel along the lead screw. To further improve the accuracy of the syringe mechanism, means are associated with the screw for preventing backlash of the screw when rotation is initiated by the motor. These means include a biased spring associated with the opposite end of the screw.

Previously, syringe mechanisms of this general type were directly connected to the slider mechanism and required precise alignment of the drive components (lead screw, traveling nut, and slider) for the operation of the plunger. Assembly of the lead screw and other drive components required precise linear alignment with no lateral misalignment which would cause errors in the volume sampled or lack of reproducibility. Even a small degree of lateral movement occurring during the rotation of the screw, whether due to misalignment of the components or from wear of the mechanism, needed to be avoided. Otherwise, variations in the precise linear movement of the plunger would be introduced.

The present invention provides a mechanism where the traveling nut is permitted to move freely in all directions except for rotation about the lead screw. Some degree of lateral misalignment of the drive components may be tolerated without that misalignment causing sampling errors. Because of the construction of the bearings between which the nut is positioned, lateral misalignment of the drive screw does not affect the precise linear movement of the slider mechanism, and consequently, the plunger. This provides a mechanism which is less expensive to assemble and align properly, but which has a high degree of accuracy and reproducibility. Further, because of the degree of freedom in the, movement of the traveling nut, less stress is placed on the syringe drive mechanism during operation.

Accordingly, it is an object of the present invention to provide a syringe drive with a lead screw mechanism of relatively simple construction which is capable of both accurate and reproducible sample volume withdrawals, including volumes of 1.0 μl or less. This, and other objects and advantages of the present invention will become apparent from the following detailed description, the accompanying drawings, and the appended claims.

BRIEF DESCRIPTION OF THE DRAWINGS

FIG. 4 is an exploded perspective view of the traveling nut and slider mechanism of the present invention;

FIG. 5 is a perspective view, partially in section, illustrating the assembly of the traveling nut and bearings into the slider mechanism; and FIG. 6 is an exploded perspective view, partially in section, of the anti-backlash spring assembly and lead screw.

DETAILED DESCRIPTION OF THE PREFERRED EMBODIMENT

Figure 1:
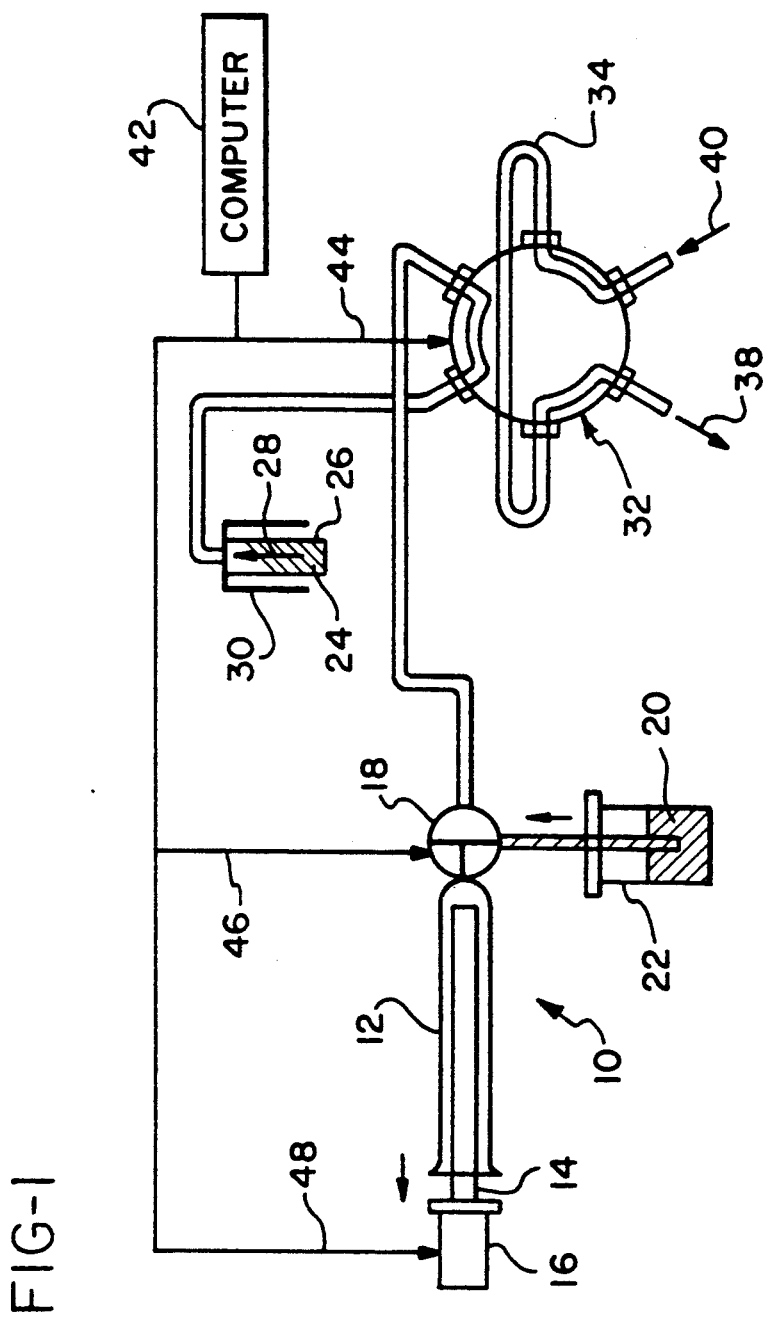
FIG. 1 is a schematic diagram of a typical liquid sampling apparatus utilizing a syringe mechanism.

Referring to FIG. 1, a typical liquid sampling apparatus 10 is illustrated having a syringe 12. Syringe 12 includes a plunger 14 movable by a drive mechanism 16 such as a stepper motor driven lead screw. A three-way valve 18 controls whether flush solvent 20 is withdrawn from reservoir 22 by the movement of plunger 14, or whether a sample 24 is withdrawn from vial 26 through needle 28 supported by sample tower 30.

The six port valve 32 has two positions, namely a "fill" position where the syringe 12 is connected to sample needle 28 via sample loop 34, and an "inject" position where the sample loop 34 is connected to a test column 38 with a fluid source for the sample by means of pump 40. For simplicity, test column 38 and pump 40 are not shown, but rather are indicated by the labeled arrows in FIG. 1. A computer 42, with associated control lines 44, 46, and 48 controls the entire system by well known methods. The operation of six port valve 32, syringe 12, and three-way valve 18 are shown to be controlled by computer 42. Further details concerning the operation of liquid sampling apparatus 10 may be found in Nohl et al, U.S. Pat. No. 4,957,009, issued Sep. 18, 1990, the disclosure of which is hereby incorporated by reference.

Figure 2:
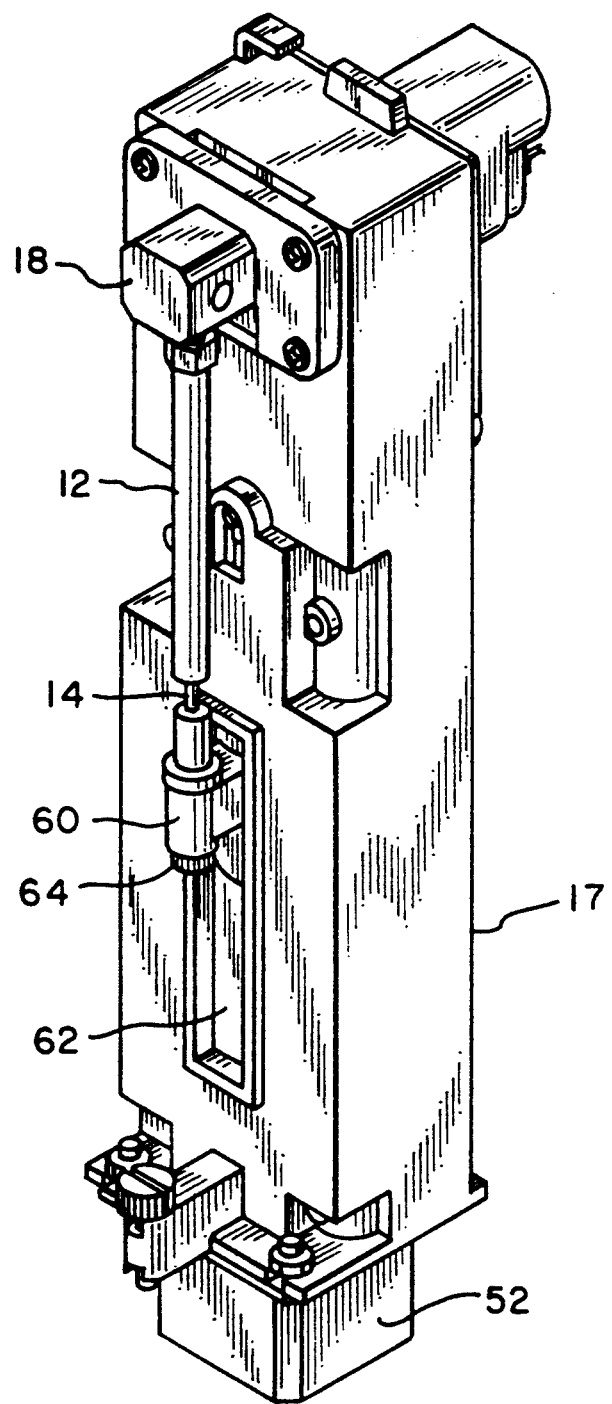
FIG. 2 is an isometric view of the syringe drive with lead screw mechanism of the present invention.
Figure 3:
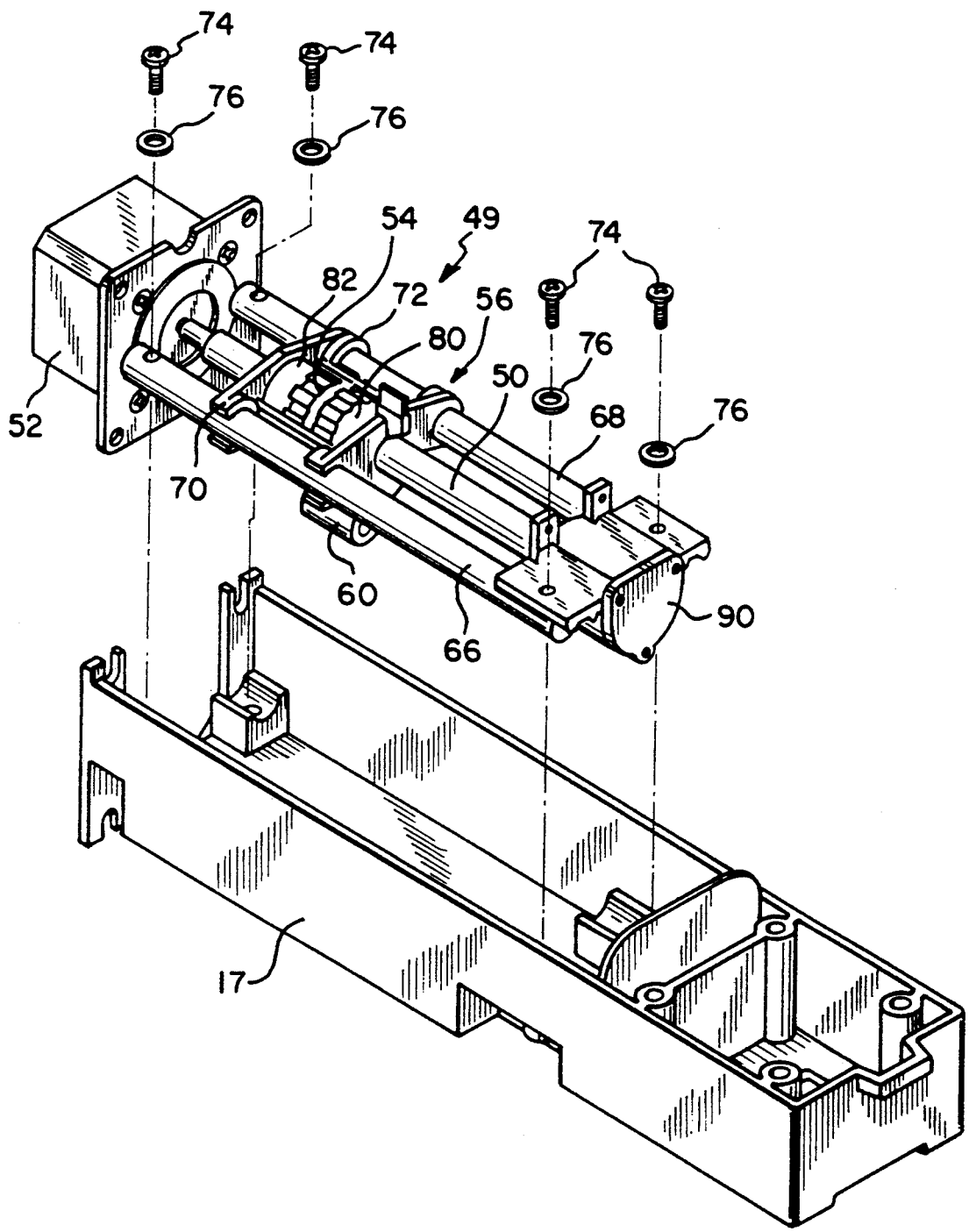
FIG. 3 is an exploded perspective view of the drive components of the present invention.

Referring now to FIGS. 2-6, the details of construction of the syringe drive with lead screw mechanism of the present invention are illustrated. As shown in FIG. 2, mounted on a housing 17, syringe 12 and plunger 14 are in communication with three-way valve 18, the position of which determines whether solvent or sample is pulled into the system. As shown in FIG. 3, the drive mechanism, generally indicated at 49, operating plunger 14 includes a threaded lead screw 50, one end of which is driven by a suitable drive means 52 such as a stepper motor. Threaded onto lead screw 50 is a traveling nut 54 which is mounted in a slider mechanism 56.

Slider mechanism 56 includes extension 60 which extends through an opening 62 in housing 17 Extension 60 includes an annular passage therein through which a thumb screw 64 extends and secures plunger 14 to slider mechanism 56. Linear movement of slider 56 translates directly into a corresponding linear movement of plunger 14.

Slider 56 is aligned for linear movement along parallel rails 66 and 68. As shown, slider 56 is slidingly secured to rails 66, 68 by suitable means such as C-shaped clips 70 and/or rings 72. The drive mechanism 49 is secured in housing 17 by suitable means such as screws 74 and washers 76.

Referring now to FIGS. 4 and 5, traveling nut 54 includes means for permitting lateral movement of the nut within slider mechanism 56. In the preferred embodiment illustrated, theses means include a pair of bearings 80 and 82 which are designed to fit over the opposite ends of nut 54. Bearings 80, 82 include annular openings therethrough for the threaded lead screw 50 to pass. The bearings have hemispherically-shaped inner surfaces which mate with the correspondingly-shaped ends of nut 54. These bearings permit the nut 54 to wobble or deviate laterally from its position within slider mechanism 56 and accommodate some misalignment or manufacturing defects in lead screw 50.

As best shown in FIG. 5, nut 54 is prevented from rotating by means of a laterally extending tab 86 which fits into a corresponding recess in extension 60 of slider mechanism 56. Thus, nut 54 is permitted to move in all directions except for rotation around threaded lead screw 50. The slider mechanism 56, nut 54, and bearings 80, 82 may all be molded from a hard plastic material such as Nylon ® or Delrin ®. Preferably, the nut and slider are of Nylon ®, while the bearings are of Delrin ®.

The syringe drive of the present invention also includes means associated with lead screw 50 for preventing backlash of the lead screw when rotation is first initiated by stepper motor 52. Backlash may affect the accuracy and reproducibility of the sample size taken. As best shown in FIG. 6, this anti-backlash means 90 includes a bearing 92 and a bias spring 94 which are positioned within housing 96. Bearing 92 reduces friction and permits free rotation of lead screw 50 within the drive mechanism. The biased spring 94 eliminates any play in the rotation of the lead screw by stepper motor 52.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A syringe drive with a lead screw mechanism for use in a sampling apparatus comprising:
   a threaded lead screw;
   means for rotating said lead screw;
   a syringe having a plunger for withdrawing a liquid sample;
   means for mechanically connecting said plunger to said lead screw, said connecting means comprising a traveling nut threaded onto said lead screw, a slider mechanism in which said nut is mounted and including means for securing said plunger thereto, means for aligning said slider mechanism for linear movement, and means for permitting lateral movement of said nut while threaded onto said lead screw relative to said slider means.

2. The syringe drive mechanism of claim 1 in which said means for rotating said lead screw comprises a stepper motor.

3. The syringe drive mechanism of claim 1 in which said means for aligning said slider mechanism comprises a pair of substantially parallel rails and means for slidably securing said slider mechanism to said rails.

4. The syringe drive mechanism of claim 1 in which said means for permitting lateral movement of said nut include at least one bearing.

5. The syringe drive mechanism of claim 4 in which said bearing includes an annular opening therein for said lead screw to pass through.

6. The syringe drive mechanism of claim 5 in which said bearing includes a hemispherical inner surface adapted to mate with a correspondingly-shaped exterior surface of said nut.

7. The syringe drive mechanism of claim 4 including a pair of bearings positioned on opposite ends of said nut.

8. The syringe drive mechanism of claim 1 including means associated with said nut for preventing rotation thereof.

9. The syringe drive mechanism of claim 8 in which said rotation preventing means comprises a tab extending laterally from said nut.

10. The syringe drive mechanism of claim 9 in which said slider mechanism includes a recess therein for receiving said laterally extending tab from said nut.

11. The syringe drive mechanism of claim 1 including means associated with said lead screw for preventing backlash of said lead screw when rotated.

12. The syringe drive mechanism of claim 1 wherein said nut is nested in said slider mechanism.

13. The syringe drive mechanism of claim 12 wherein;
   said syringe drive mechanism includes means associated with said nut for preventing rotation thereof, said rotation preventing means comprising a tab extending laterally from said nut; and
   said slider mechanism includes a recess therein for receiving said laterally extending tab from said nut.

14. The syringe drive mechanism of claim 12 wherein said means for permitting lateral movement of said nut includes two bearings, each bearing including an annular opening therein for said lead screw to pass through and a hemispherical inner surface adapted to mate with correspondingly-shaped exterior surfaces at opposite ends of said nut.

15. The syringe drive mechanism of claim 1 wherein means for permitting lateral movement of said nut permits said traveling nut to move freely through a limited range in all directions relative to said slider mechanism except the direction said nut travels along said lead screw.

16. The syringe drive mechanism of claim 1 wherein means for permitting lateral movement of said nut permits limited rotational motion of said nut and said lead screw about at least one axis perpendicular to the longitudinal axis of said lead screw.

17. A syringe drive with a lead screw mechanism for use in a sampling apparatus comprising:
   a threaded lead screw;
   means for rotating said lead screw;
   a syringe having a plunger for withdrawing a liquid sample;
   means for mechanically connecting said plunger to said lead screw, said connecting means comprising a full traveling nut threaded completely onto said lead screw, a slider mechanism in which said nut is mounted and including means for securing said plunger thereto, means for aligning said slider mechanism for linear movement, and means for permitting lateral movement of said nut relative to said slider mechanism.

18. A syringe drive with a lead screw mechanism for use in a sampling apparatus comprising:
   a threaded lead screw;
   means for rotating said lead screw;
   a syringe having a plunger for withdrawing a liquid sample;
   means for mechanically connecting said plunger to said lead screw, said connecting means comprising a traveling nut threaded onto said lead screw for longitudinal travel only relative thereto, a slider mechanism in which said nut is mounted and including means for securing said plunger thereto, means for aligning said slider mechanism for linear movement, and means for permitting lateral movement of said nut and lead screw.

* * * * *